United States Patent [19]
Sperling et al.

[11] Patent Number: 5,786,425
[45] Date of Patent: Jul. 28, 1998

[54] PROCESS FOR PRODUCING BIOCOMPATIBLE POLYISOPRENE-POLYURETHANE INTERPENETRATING POLYMER NETWORK COMPOSITIONS FOR USE IN MEDICAL DEVICES AND THE LIKE

[75] Inventors: Leslie H. Sperling, Bethlehem; Clarence J. Murphy, Stroudsburg; Vinay Mishra, Bethlehem, all of Pa.

[73] Assignee: Schneider (USA) Inc., Plymouth, Minn.

[21] Appl. No.: 878,167

[22] Filed: Jun. 18, 1997

Related U.S. Application Data

[62] Division of Ser. No. 197,030, Feb. 16, 1994, abandoned.

[51] Int. Cl.[6] .................... C08L 75/04; C08L 75/06; C08L 75/08
[52] U.S. Cl. .................... 525/131; 525/95; 525/127; 525/130; 525/333.2; 525/385; 525/387; 525/903
[58] Field of Search ............ 525/903, 127, 525/130, 131

[56] References Cited

U.S. PATENT DOCUMENTS

| 3,980,595 | 9/1976 | Schonfeld. | |
| 5,087,514 | 2/1992 | Graefe | 428/315.5 |
| 5,162,414 | 11/1992 | Hung | 524/345 |

OTHER PUBLICATIONS

R.J. Lewis, Sr., "Hawley's Condensed Chemical Dictionary", 12th Ed., (1993)935,936,1131, Van Nostrand (New York).

*Primary Examiner*—Fred Zitomer
*Attorney, Agent, or Firm*—Peter C. Richardson; Lawrence C. Akers; Howard R. Jaeger

[57] ABSTRACT

Interpenetrating polymer networks (IPN's), composed of polyisoprene (PI) and polyurethane (PU), together with a process for their preparation and their use in the manufacture of medical devices, such as catheters and catheter balloons, are disclosed. Both components are elastomers. The PI component is chemically crosslinked. The PU component is crystallizable and contains only physical crosslinks. The IPN's have glass transition temperatures in the range of from −65° C. to −40° C.

15 Claims, 5 Drawing Sheets

PROCESS FOR PRODUCING BIOCOMPATIBLE POLYISOPRENE-POLYURETHANE INTERPENETRATING POLYMER NETWORK COMPOSITIONS FOR USE IN MEDICAL DEVICES AND THE LIKE

This is a division, of application Ser. No. 08/197,030, filed on Feb. 16, 1994 abandoned.

BACKGROUND OF THE INVENTION

This invention relates to materials comprising a network and a linear polymer. More particularly, it relates to semi-interpenetrating polymer networks. Still more particularly, it relates to semi-interpenetrating polymer networks based on two elastomers.

An interpenetrating polymer network (IPN) is any material containing two polymers, each in network form, at least one of which is synthesized and/or crosslinked in the immediate presence of the other. An IPN is distinguishable from simple polymer blends, blocks, and grafts in that an IPN swells, but does not dissolve in solvents, and the properties of creep and flow are suppressed in an IPN.

There are five principal types of IPN's, namely, a sequential IPN, which is formed by initially synthesizing and cross-linking a first polymer from its monomer and an appropriate crosslinker and initiator, followed by the addition of a second monomer and an appropriate crosslinker and initiator, all of which are swollen into the first polymer and polymerized in situ; a simultaneous interpenetrating network (SIN), the synthesis of which begins with a mutual solution of both monomers and their respective crosslinkers, which are then polymerized simultaneously in non-interfering modes, such as by stepwise and chain polymerizations; an interpenetrating elastomeric network (IEN), synthesized from two latexes of linear polymers, which are mixed and coagulated, and wherein both components are simultaneously crosslinked; a gradient IPN, in which the overall compositions or crosslink density of the material varies from one location to another; and a thermoplastic IPN, which is a hybrid between a polymer blend and an IPN, containing physical rather than chemical crosslinks.

In situations where only one of the two polymers is crosslinked, and the other is linear, the polymer is called a semi-IPN structure. If the polymerizations occur sequentially in time, there are four possible semi-IPN's. When polymer I is crosslinked and polymer II is linear, then the product is called a semi-IPN of the first kind, or semi-I; when polymer I is linear and polymer II is crosslinked, the product is called a semi-IPN of the second kind, or semi-II. In the remaining two types of semi-IPN's, the older or polymerization of the two components is reversed.

Where polymerization of the two components occurs simultaneously, only two semi-IPN's, or semi-SIN's are distinguishable. In yet another type of IPN, called "thermoplastic IPN's", the chemical crosslinks are replaced by physical crosslinks, e.g., the crystallites in semi-crystalline polymers, the ionic portions of ionomers, etc.

The network structure of an IPN may be the result of either chemical crosslinks from covalent bonding among the polymer molecules, or physical crosslinks, the result of crystalline, glassy or ionic phase domains which contain multiple segments of polymer chains. While most IPN's do not interpenetrate at the molecular level, when properly engineered they may form finely divided phase domains in the nanometer size range. These phases may interpenetrate one another, forming dual-phase continuity where the two or more phases are continuous on a macroscopic level. The co-continuous phase behavior of IPN's is often responsible for their unique properties.

Most IPN's, regardless of the method of their formation, phase separate. As monomers polymerize, miscibility decreases, resulting in phase separation. Since crosslinking reduces phase separation and, in particular, reduces domain size, it often results in finely dispersed phase domains ranging in size from about 10 to about 100 nm. The kinetics and extent of crosslinking and phase separation have great influence over the phase morphology. In this way, IPN's can resemble polymer "alloys", where polymer blends may be made chemically compatible in order to achieve a desired phase morphology.

By mixing two immiscible polymers, various phase morphologies may be formed. The morphology depends on the volume fraction of the components, the shear viscosity of the phases, the amount of interfacial compatibility and the relative rates of crosslinking and phase separation. One or both of the two polymers can be crosslinked during or after the mixing, forming an IPN.

One typical morphology shows droplets dispersed in a continuous matrix. This morphology is observed in rubber-toughened plastics where the matrix is brittle and the droplets are rubber. Another typical morphology shows dispersed fibers. This morphology is frequently observed in liquid crystal polymers and some thermoplastic elastomers. In IPN's with a co-continuous morphology, the two phases are actually interlocked or are interpenetrating.

The phase morphology of an IPN before or during crosslinking is a complicated function of many variables, however, the phase continuity is governed primarily by the volume fraction $v$ and viscosity $\eta$ of each phase. These parameters are related by the expression:

$$\frac{v_1}{v_2} \times \frac{\eta_2}{\eta_1} \quad \begin{cases} >1 & = \text{phase 1 continuous} \\ \approx 1 & = \text{co-continuous phases} \\ <1 & = \text{phase 2 continuous} \end{cases} \quad (1)$$

Where subscripts 1 and 2 denote phases 1 and 2, respectively.

Several important physical property characteristics result from co-continuous phase morphology. When microheterogeneous phase domains are in the range of from about 10 to about 20 nm, the whole material is essentially interphase material. Consequently, the glass transitions tend to be very broad, covering the range between those of the two component polymers. This very broad glass transition leads to materials that can absorb energy or are useful as damping materials over a broad temperature and frequency range. The co-continuous nature of IPN's can lead to materials having a toughness greater than either of the constituent polymers.

The fields of polyurethanes and polyurethane-based interpenetrating polymer networks (IPN's) has had many important advances in recent years. There are several classes of the polyurethanes: some are used in foams, others make outstanding fibers. A particularly interesting class of the polyurethanes is the so-called segmented elastomers, which are a type of multiblock copolymer. These materials usually contain a polyether or polyester elastomeric block alternating with a urethane linkage. The elastomeric block is frequently made so that it crystallizes on extension, providing a certain degree of self-reinforcement. Polyurethane materials have been used in numerous industrial and commercial applications. In the medical field, for example, applications have included medical grade tubing, and catheter balloons.

A polyurethane may serve as network I in a sequential IPN synthesis, or in prepolymer form as one component of simultaneous interpenetrating networks (SIN's). Meyer et al., (*Polymer*, V. 24, p. 1415 (1983) and *Eur. Polym. J.*, V. 19, p. 597 (1984)) investigated compositions based on cross-polyurethane-inter-cross-poly(methyl methacrylate) (PMMA). In general, the synthesis involved an aromatic triisocyanate and a polyether glycol. The PMMA network resulted from an AIBN-initiated free radical polymerization with a trimethacrylate crosslinker. The resulting IPN's exhibited two loss peaks in the tan δ-temperature studies, but the glass transitions were shifted inward significantly, with broadening. This inward shifting of the glass transition temperature ($T_g$) indicates a certain extent of molecular mixing. Jin and Meyer (*Polymer*, V. 27, p. 592 (1986)) studied the kinetics of reaction of these IPN's. Other work in polyurethane-based IPN's and SIN's has been done by Frisch et al., (*Pure Appl. Chem.*, V. 53, p. 1557 (1981)), Hourston et al., (*J. Appl. Polym. Sci.* V. 45, p. 1753 (1992)), Allen et al., (*Polymer*, V. 14, p. 597 (1974)), Klempner et al., (*J. Appl. Polym. Sci.*, V. 32, p. 4197 (1986)).

Each of these previously synthesized IPN's or SIN's was made with an elastomeric polyurethane and a rigid plastic, usually either poly(methyl methacrylate) or polystyrene. Up to this time, few IPN's or SIN's have been made where both components are elastomeric. Research in this area has been limited, resulting in a lack of information regarding the stress-strain behavior of an elastomer-elastomer IPN and the effects of crystallization on the mechanical behavior of the IPN or SIN.

In the medical arts, there is a need for materials having both high extension and high tensile strength for use in the manufacture of medical devices such as catheters, tubing, films, balloons, and the like.

We have discovered a novel composition of matter that is a semi-IPN based on elastomeric polyurethanes and cis-polyisoprene, which is a material ideally suited for these needs.

The present invention relates to IPN's based on polyurethanes and cis-polyisoprene. Both components of these IPN's are elastomeric, with $T_g$'s lying in the range –65° C. to –40° C. In the present system, only one component, cis-polyisoprene, contains chemical crosslinks. The polyurethane component is crystallizable and hence, contains physical crosslinks.

DETAILED DESCRIPTION OF THE INVENTION

Any elastomeric polyurethane (PU) can be utilized as the polyurethane component of the IPN compositions according to the present invention. In particular, however, we have found that polyether-based thermoplastic polyurethanes (TPU's) produce the best results. Two examples of such TPU product lines which have been utilized are Elastollan (MP-100) (BASF Corporation) and Morthane (PE 90–100) (Morton International, Inc.). The PU component is crystallizable and forms only physical crosslinks. These two products are approved for medical use as USP Class VI materials.

Although any polyisoprene (PI) is utilizable as the PI component, a linear PI is preferred. Linear cis - 1,4 PI was utilized as the PI component (Aldrich Chemical Company). The PI component of the semi-IPN's according to the present invention form chemical crosslinks.

IPN's synthesized utilizing the above PU and PI components form semi-IPN's, since only the PI component is chemically crosslinked.

A peroxide, such as benzoyl peroxide or dicumyl peroxide is used as a polymerization crosslinking initiator. Benzoyl peroxide (BPO) and dicumyl peroxide (Dicup) (both, Aldrich Chemical Company) were utilized as initiators.

Semi-IPN's of PI and PU formed according to the present invention have compositions wherein the PI and PU are present in a ratio of from about 1:99 to about 99:1, by weight. The preferred range of ratio of PI to PU in the semi-IPN compositions according to the present invention is from about 10:90 to about 40:60, by weight.

The final blended product becomes crosslinked on molding. Most of the chemical crosslinks are formed in the PI, although a lower level of crosslinking also takes place in the TPU. TPU's are often slightly crystalline, thereby enabling them to also undergo physical crosslink formation, resulting in higher modulus and greater strength in the semi-IPN.

Tetrahydrofuran (THF) (Fisher Scientific Company) was utilized as the solvent.

Mixing of the components can be accomplished utilizing any suitable means. A Brabender® mixer is preferred.

The PU component is plasticized to lower its viscosity and allow melt blending with the PI. The THF solvent is then removed.

Compositions were synthesized by blending the cis-PI and a TPU with a peroxide, followed by compression molding at an elevated temperature to crosslink the PI, forming a network.

BPO was utilized as the peroxide together with the Elastollan TPU and Dicup was utilized as the peroxide with the Morthane TPU.

Compositions utilizing the Elastollan TPU were synthesized by the following procedure. Solutions of PI and Elastollan TPU were prepared in THF solvent with approximately 15% polymer (by weight). Prior to mixing with THF, the PI was masticated in a Brabender mixer at 120° C. for 10 minutes in accordance with the mastication process for natural rubber. BPO initiator was added to the PI solution (1.0% of PI). The two polymer solutions were mixed using vigorous stirring in predetermined proportions and poured into silicone-coated molds. The solution in the mold was degassed in a vacuum chamber to remove the air that was dissolved and trapped during the mixing step. The THF solvent was removed by evaporation (usually requiring 70–80 hours). Approximately 10 cm×10 cm films were prepared in thicknesses ranging from 0.9 to 2.1 mm. The polymer films obtained were kept in a vacuum chamber for 90–100 hours to remove any residual THF. The films were compression molded at 120° C. for 15 minutes to crosslink the PI component.

Table 1 shows several compositions of semi-IPN's formed according to the present invention utilizing Elastollan MP-100 TPU as the PU component.

TABLE I

Elastollan Series Formulations

| Sample No. | Composition: PI/Elastollan ratio | Benzoyl Peroxide (% on PI) |
|---|---|---|
| 1 | 0/100 | 1.0 |
| 2 | 10/90 | 1.0 |
| 3 | 20/80 | 1.0 |
| 4 | 30/70 | 1.0 |
| 5 | 40/60 | 1.0 |
| 6 | 100/0 | 1.0 |

Compositions utilizing the Morthane TPU were synthesized by the following procedure. Morthane TPU was processed in a Brabender mixer at 120° C. at 50 RPM. A small quantity of THF was added (approximately 10% on Morthane) to plasticize the TPU. After 10 minutes, PI was added in predetermined proportions and the blending continued for another 10 minutes. Finally, the Dicup initiator was added as a 10% solution in THF and the mixing continued for 10 more minutes. The mixture of Morthane, PI, dicup and THF was compression molded to form films. Approximately 10 cm×10 cm films were prepared in thicknesses ranging from 0.9 to 2.1 mm. The films were compression molded at 145° C. for 90 minutes to crosslink the PI component. Most of the THF is evaporated during this step. The films were kept in a vacuum chamber for 60–70 hrs to ensure complete removal of THF.

Table II shows several compositions of semi-IPN's formed according to the present invention utilizing Morthane PE 90-100 as the TPU PU component.

TABLE II

Morthane Series Formulations

| Sample No. | Composition: PI/Morthane ratio | Dicumyl Peroxide (% on Total Weight) |
|---|---|---|
| 7 | 0/100 | 1.0 |
| 8 | 10/90 | 1.0 |
| 9 | 20/80 | 1.0 |
| 10 | 30/70 | 1.0 |
| 11 | 40/60 | 1.0 |
| 12 | 100/0 | 1.0 |

The various polymer films synthesized utilizing both the Elastollan TPU and the Morthane TPU were characterized utilizing the following procedure. Mechanical testing of all materials was done at room temperature (25° C.) on an Instron Testing Machine (Frame 1011) using a 5000 Newton load transducer. Microtensile test specimens were used for all samples. The specimens had gage lengths of about 16.8 mm, and widths of about 4.8 mm (except for sample nos. 7 and 12, for which, the gage lengths were 33.6 mm and the width 6.3 mm). A constant strain rate of about 150%/min was used for all samples (the crosshead speeds were 25 mm/min for samples with gage length 16.8 mm, and 50 mm/min for those with the gage length 33.6 mm). A minimum of two specimens were used for each composition. Results of mechanical testing of all samples based on both the Elastollan TPU and the Morthane TPU are shown in Table III.

TABLE III

Mechanical Characterization of Elastollan- and Morthane-Series IPN's.

| Sample No. | % PI | Young's Modulus (MPa) | Strain at break | Tensile Strength (eng.) (MPa)† | Tensile Strength (true) (MPa)† | Toughness (MJ/m³) |
|---|---|---|---|---|---|---|
| 1 | 0 | 18.2 | 8.1 | 50 | 457 | 147 |
| 2 | 10 | 13.8 | 9.7 | 38 | 407 | 140 |
| 3 | 20 | 12.2 | 8.0 | 29 | 261 | 92 |
| 4 | 30 | 10.0 | 7.7 | 19 | 165 | 60 |
| 5 | 40 | 8.3 | 7.3 | 11 | 91 | 38 |
| 6* | 100 | — | 7.1 | — | — | — |
| 7 | 0 | 10.0 | 8.2 | 27 | 246 | 110 |
| 8 | 10 | 8.6 | 10.3 | 30 | 339 | 135 |
| 9 | 20 | 5.9 | 9.5 | 17 | 179 | 74 |
| 10 | 30 | 5.5 | 9.9 | 16 | 174 | 67 |
| 11 | 40 | 4.1 | 9.2 | 16 | 163 | 57 |
| 12 | 100 | 0.6 | 14.5 | 5 | 78 | 22 |

*The load required to pull sample No. 6 was too small to be accurately determined by the load transducer used.
† 1 MPa = 145 psi.

A Mettler TA-3000 Differential Scanning Calorimeter (DSC) was used to determine the glass transition behavior of the IPN's and the homopolymers. Each sample was quenched from room temperature to −150° C. and maintained at that temperature for 2 minutes after which it was heated at a rate of 20° C./min under a nitrogen atmosphere.

A Gehman torsional stiffness tester was used in accordance with ASTM-D1053- 85 to determine the modulus-temperature behavior of selected compositions from the Morthane series. The sample was held in a stainless-steel Dewar flask filled with air cooled by liquid nitrogen and the whole apparatus allowed to warm up at the rate of about 1–3° C./min. The modulus calculated from a 10-second relaxation is reported.

Extraction experiments were conducted in THF in order to determine the soluble fractions of the IPN's. Total swelling was also recorded. A Brabender mixer was used to estimate the melt viscosities of the linear homopolymers Morthane and cis-polyisoprene. The Brabender measures the torque needed to process a given polymer at a given temperature which can be converted to viscosity units by using the empirical equation developed by Goodrich and Porter.

Figure 1:
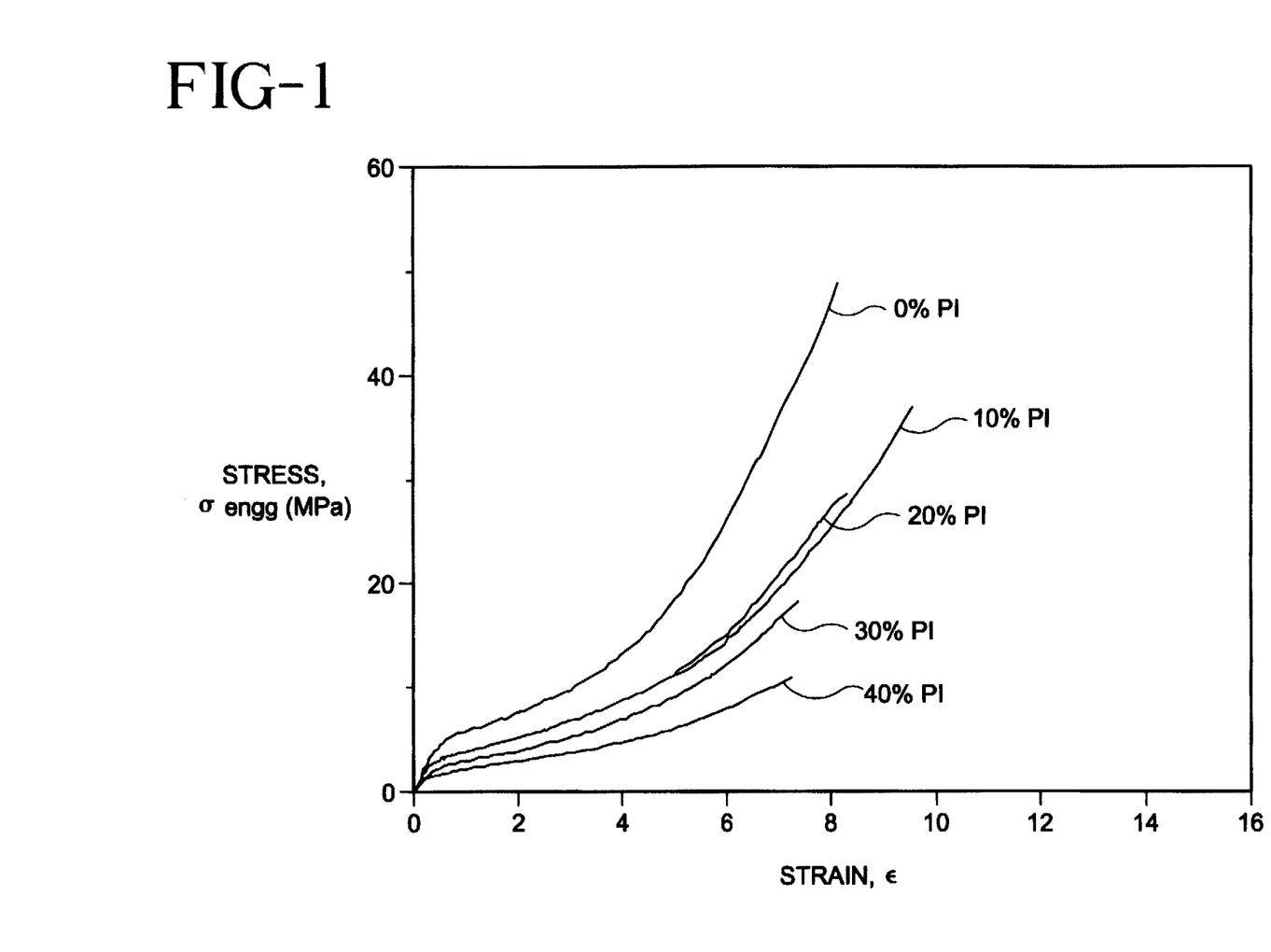
FIG. 1 is an engineering stress vs. strain plot for IPN samples based on Elastollan TPU and cis-PI.
Figure 2:
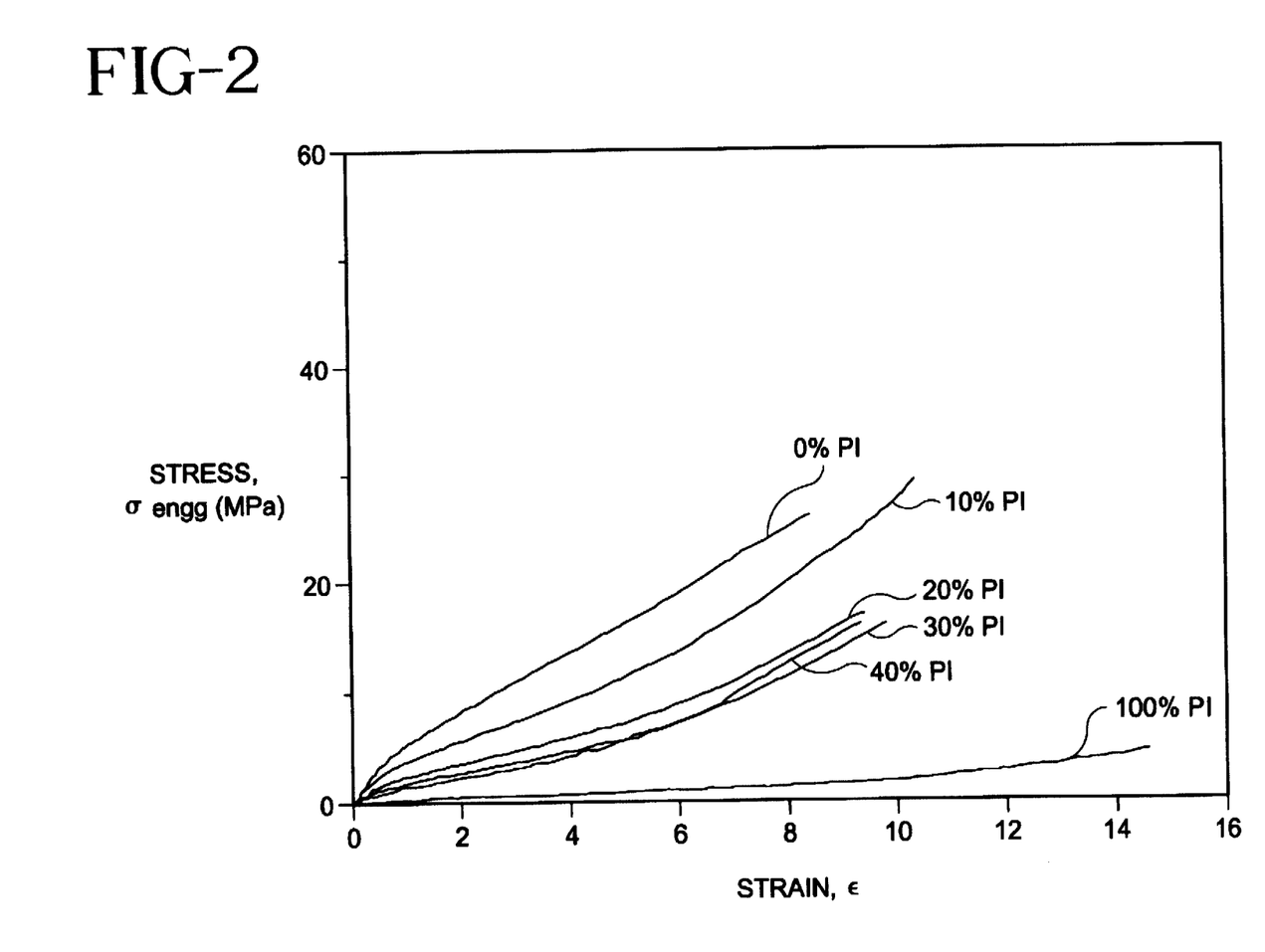
FIG. 2 is an engineering stress vs. strain plot for IPN samples based on Morthane TPU and cis-PI.

Representative stress-strain plots for each of the compositions are shown in FIGS. 1 and 2. It was found that the 10%-PI composition in the Elastollan TPU series has an elongation to break higher than that for either of the two homopolymers. In the Morthane TPU series, the elongation to break for all compositions prepared is greater than the value for the parent polyurethane, but less than that for the pure cis-PI of the same series.

The curves shown in FIGS. 1 and 2 are of engineering stress ($\sigma_{eng}$) vs. strain, i.e., the load is divided by the initial cross-sectional area. Percentage PI in each sample in FIGS. 1 and 2 are shown along with their curves. Samples in FIG. 1 were crosslinked using 1.0% benzoyl peroxide initiator based on the mass of PI. Samples in FIG. 2 were crosslinked using 1.0% dicumyl peroxide initiator based on the total mass (PI+Morthane). Since all these materials undergo a very large strain at the time of rupture, the cross-sectional area of a sample is reduced by a large fraction. Therefore, the tensile strength was obtained by using the final cross-sectional area, i.e., calculating the true stress ($\sigma_{true}$) Table III shows both engineering and true stress values for the tensile strengths. The relation between the two is given by the following equation:

$$\sigma_{true} = \sigma_{eng}(1+\epsilon) \quad (2)$$

where $\epsilon$ is the strain at the break point.

Figure 3:
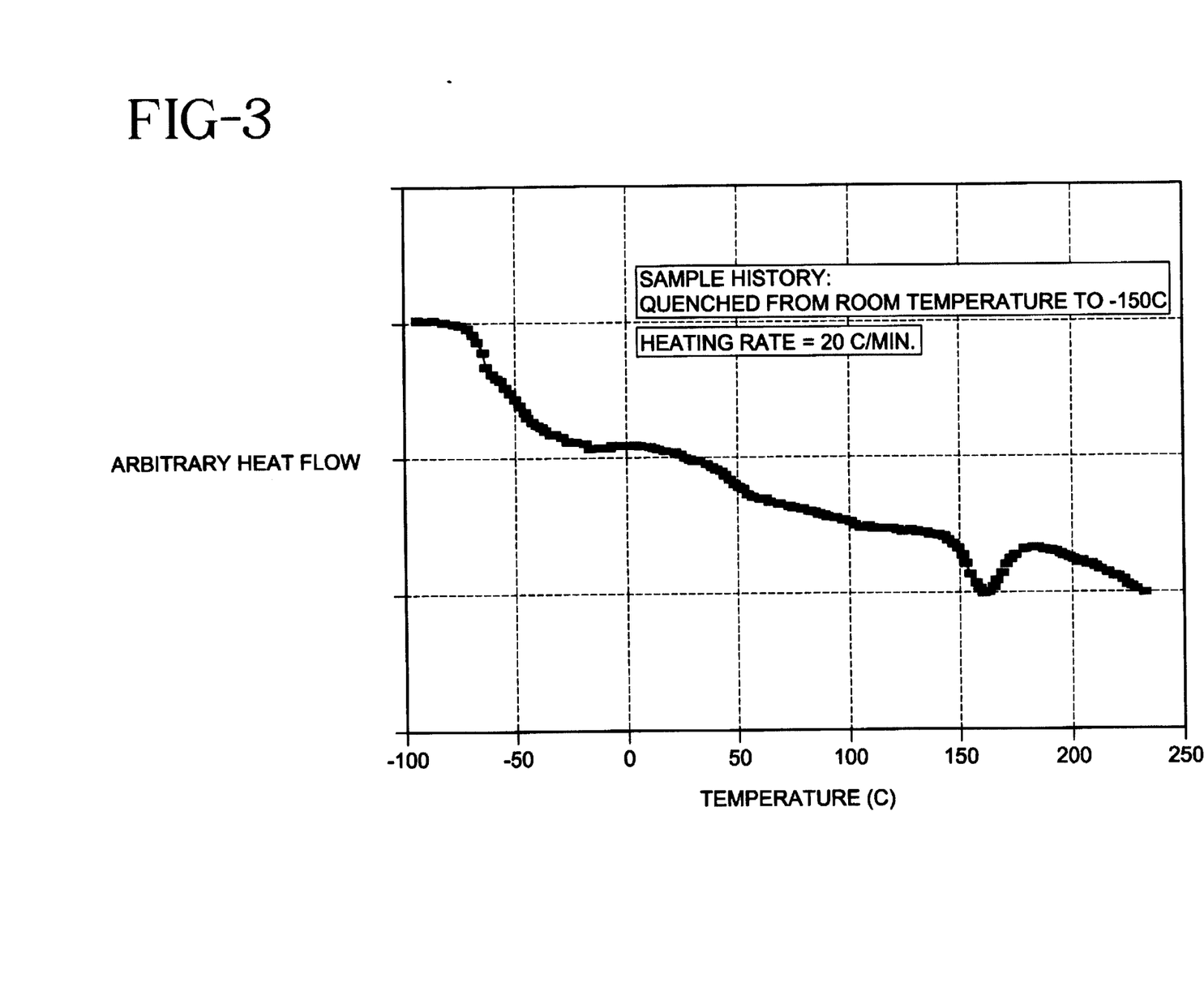
FIG. 3 is a differential scanning calorimetry scan of a sample of an IPN based on Morthane TPU and cis-PI.
Figure 4:
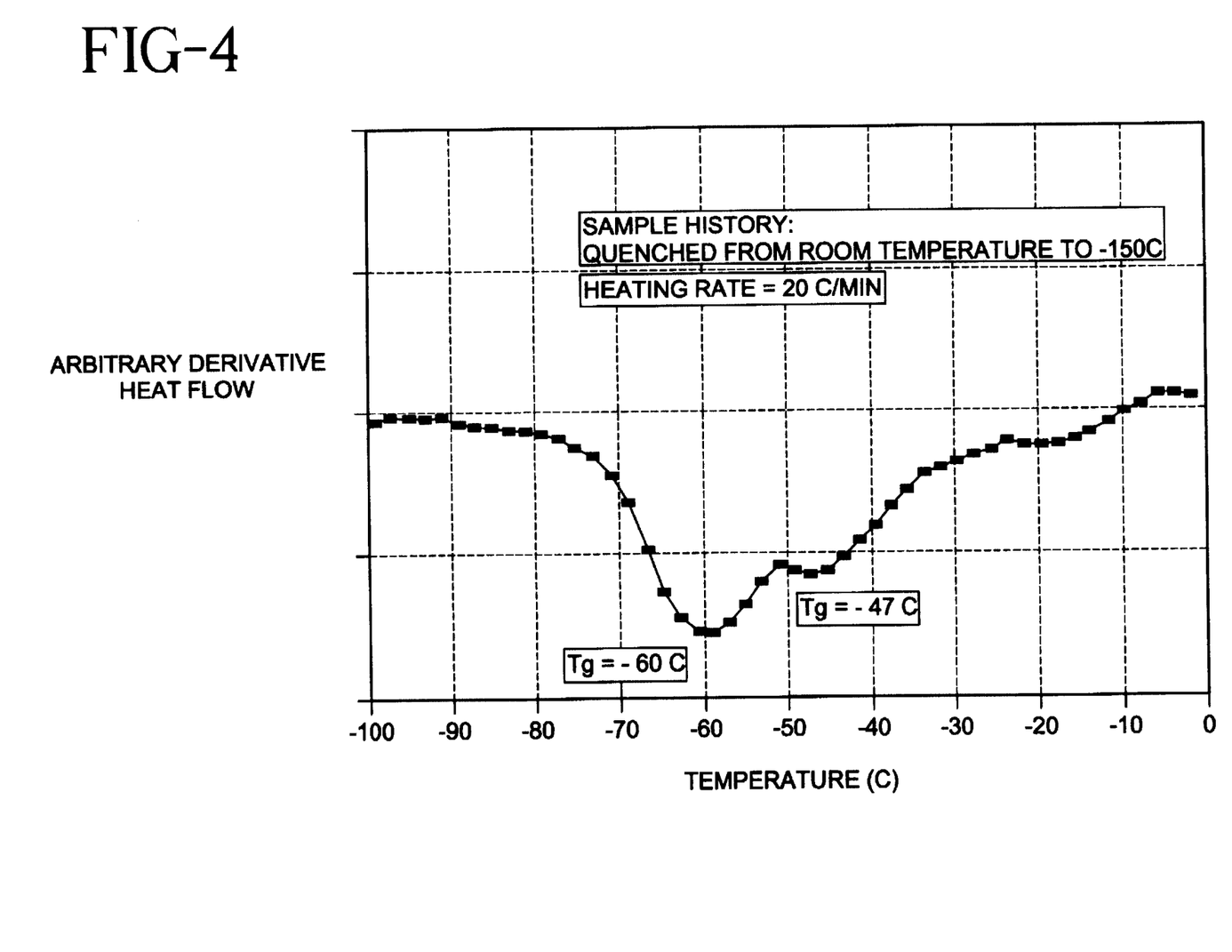
FIG. 4 is a plot of derivative heat flow vs. temperature for the data of FIG. 3 showing the primary glass-transitions ($T_g$'s).

Results of a typical DSC scan are shown in FIG. 3 for the 30%-PI sample from the Morthane TPU series (sample #10). The sample contained 30% PI and was crosslinked using 1.0% dicumyl peroxide initiator based on the total mass (PI+Morthane). The $T_g$ for pure PI occurs at −62° C. For pure Morthane TPU, a segmented polyurethane, the primary $T_g$ occurs at −46° C. (due to its soft polyether segment). The semi-crystalline hard segment of Morthane melts between 145°–180° C. and goes through a faint secondary $T_g$ at 50° C. Since the primary $T_g$'s for the two pure polymers are very close, it is difficult to identify them separately in the normal DSC plots (heat flow vs. temperature). A plot of "derivative heat flow" vs. temperature indicates each $T_g$ as an inverted peak. (The lowest point of such a peak is taken as the glass transition temperature. In the normal DSC plot, this point refers to the temperature at the point of steepest slope in the glass transition region.) In FIG. 4, each of the two glass-transitions for sample #10 is seen quite distinctly, which indicates the two-phase nature of these materials. Combining this information with the optical clarity of these materials hints towards a microheterogeneous morphology. DSC results also show faint shifts in the two individual $T_g$ (1°–2° C.) indicating little or no mixing between the two components of the IPN's at the molecular level.

Figure 5:
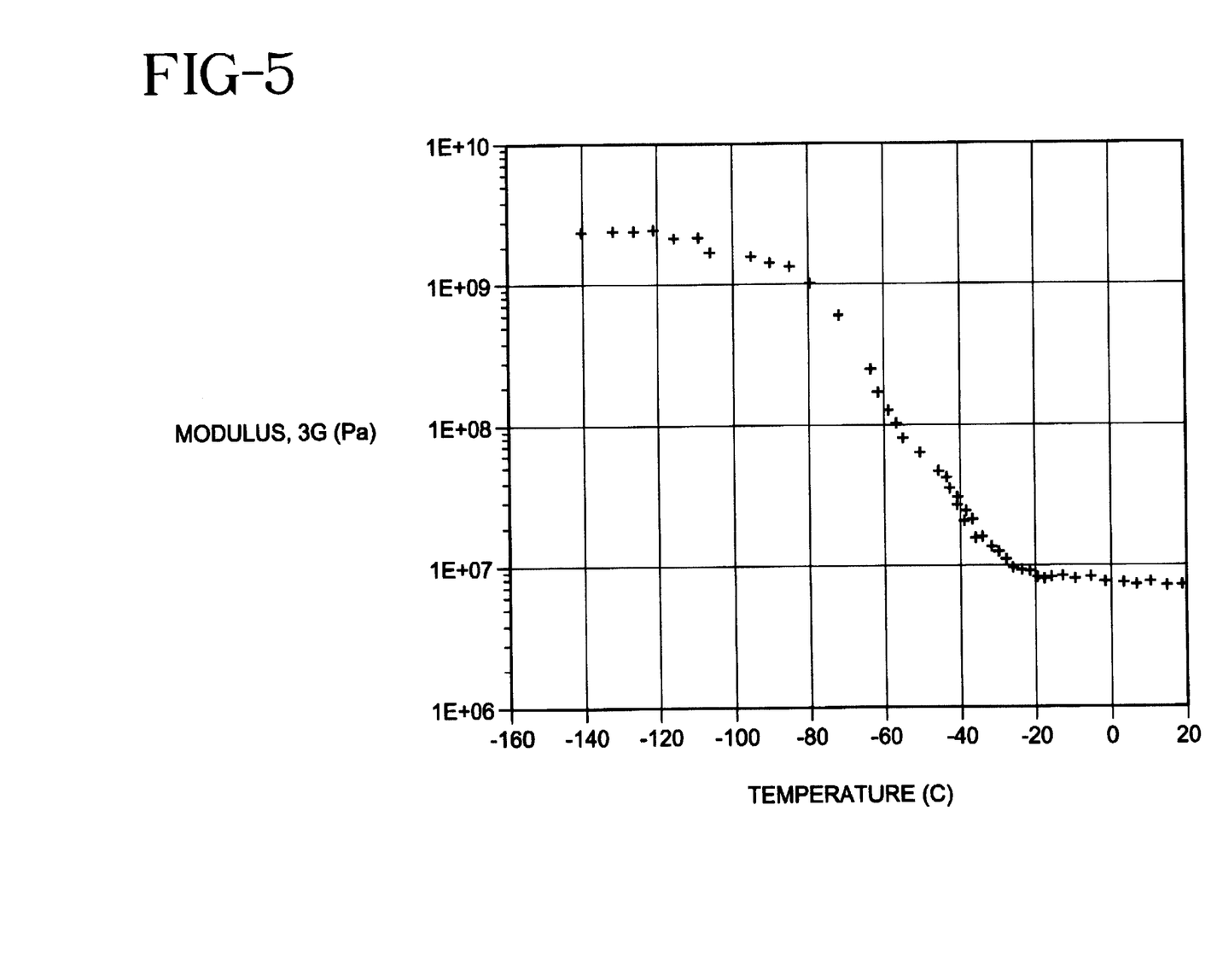
FIG. 5 is a plot of Young's Modulus vs. temperature behavior of a sample of an IPN based on Morthane TPU and cis-PI.

Young's modulus-temperature behavior of sample no. 10 (Morthane TPU series, 30%-PI) as obtained from the Gehman torsional stiffness tester is shown in FIG. 5 (The Gehman experiment yields the shear modulus G; for elastomers, Young's modulus, E, is approximately 3 times the shear modulus, G; e.g. E≈3G). The sample contained 30% PI and was crosslinked using 1.0% dicumyl peroxide initiator based on the total mass (PI+Morthane). Once again, the small difference in the two primary $T_g$'s in the sample renders them indistinct. The Young's modulus on this sample at room temperature is $7 \times 10^7$ dynes/cm² (7 MPa). The Young's modulus on the same sample determined on the Instron is substantially lower, 5.5 MPa (see Table 11).

Results from swelling studies in THF for the Morthane TPU series are shown in Table IV.

TABLE IV

Swelling and Extraction Studies
on Morthane-Series IPN's using THF Solvent

| Sample No. | % PI | % Morthane | Equilibrium Polymer Volume Fraction, $v_2$ | % Solubles |
|---|---|---|---|---|
| 7 | 0 | 100 | 0.07 | 69.9 ± 2.3 |
| 8 | 10 | 90 | 0.13 | 80.0 ± 0.8 |
| 9 | 20 | 80 | 0.12 | 68.1 ± 3.2 |
| 10 | 30 | 70 | 0.12 | 65.7 ± 1.6 |
| 11 | 40 | 60 | 0.13 | 53.8 ± 0.3 |
| 12 | 100 | 0 | 0.10 | 3.4 ± 1.7 |

Since PI is the main component chemically crosslinked, the percentage of solubles increases as the percentage of Morthane increases in the sample. However, the 0% PI (100% Morthane) sample is not completely soluble which indicates that the some cross-linking is introduced in the polyurethane component too, possibly by a hydrogen-abstraction mechanism. The 100%-PI sample (no. 12) has a soluble fraction of less than 4%. The number of network chain segments per cm³, n, as calculated using the Flory-Rehner equilibrium swelling theory is $n = 1 \times 10^4$ moles/cm³. Using the rubber elasticity equation:

$$E = 3nRT, \quad (3)$$

where R is universal gas constant and T the absolute temperature in degrees Kelvin, this predicts a modulus of 0.8 MPa at room temperature (25° C.) which is somewhat higher than the Instron-determined modulus, 0.6 MPa (see Table III).

The crosslink-density for the 100%-PI sample from the Elastollan series (sample no. 6) is calculated as $n = 1 \times 10^5$ moles/cm³. [Equation (3) predicts a modulus 0.08 MPa at room temperature (25° C.).] The other samples of this series disintegrated when immersed in THF.

Torque measurements on the cis-PI and Morthane TPU polymers yield their melt viscosities at 145° C. These values are shown in Table V.

TABLE V

Melt-Viscosity from Brabender Torque Measurements
for cis-PI and Morthane

| Polymer | RPM, S | Torque, M (meter-grams) | Viscosity, n* (Pa-s) |
|---|---|---|---|
| Cis-PI | 50 | 1,800 | 1,620 |
| Morthane | 50 | 2,300 | 2,070 |

*1 Pa-s = 10 poise
Operating temperature = 145° C.

The following relation was used:

$$\eta(\text{poises}) = 450 \frac{M(\text{meter-grams})}{S(\text{rpm})}, \quad (4)$$

where $\eta$ is the melt viscosity of the polymer, M the torque as read by the Brabender, and S the rpm of Brabender operation. The torque read from the instrument at 20 minutes from the start was used: 2300 meter-grams for Morthane and 1800 meter-grams for cis-PI respectively (both at S=50 rpm).

Thus, the ratio of the melt viscosities of cis-PI and Morthane is roughly 0.78. This means that for dual-phase continuity characteristics in the IPN's, the ratio of the volume fractions of these two polymers should be close to 1:1.

Two series of semi-interpenetrating polymer networks were prepared using two TPU's and cis-1,4 PI in compositions 10–40% PI. The PI component was chemically crosslinked using a free radical initiator. The crosslink-density in the Elastollan TPU series was an order of magnitude lower than that in the Morthane TPU series ($10^5$ vs. $10^4$ moles/cm³). Swelling tests show that some crosslinking is also introduced in the polyurethane component along with the crosslinking in the PI component.

Synergistic behavior was observed in mechanical properties for the 10%-PI compositions in both series. DSC data shows the dual-phase characteristic of the IPN's with little or no mixing at the molecular level. Their phase-separated nature, combined with the optical clarity suggests a microheterogeneous morphology.

Although the degree of chemical crosslinking in the polyurethane component is low, there is a significant "degree of physical crosslinking" owing to its semi.13 crystalline hard segments. In this respect, these compositions have structures intermediate between thermoplastic IPN's and full IPN's.

The PI-PU semi-IPN's having the abovedescribed compositions are biocompatible compositions. Sheets or films of the material are useful in the fabrication of medical devices such as catheters, catheter balloons, and the like.

EXAMPLES

Preparation of interpenetrating Polymer Network (IPN) Based on Polyisoprene (PI) and Polyurethane (PU)

Example 1—Based on Morthane TPU

A polyisoprene-polyurethane interpenetrating polymer network (PI-PU IPN), having a ratio of PI to PU of about 1:9 by weight was prepared as follows:

Into a Brabender® mixer, preheated to 120° C., was charged 46.0 gm of polyurethane (Morthane® PE 90–100, Morton International, Inc.) and 5 ml tetrahydrofuran (THF) (Fisher Scientific Company), followed by mixing at 50 rpm for 15 minutes with the lid in place on the mixing chamber. To the mixer was then charged 5.1 gm linear cis-1,4-polyisoprene (Aldrich Chemical Company), with further mixing for 15 minutes at 50 rpm with the mixing chamber covered. To the mixer was then charged 0.51 gm Dicup (dicumyl peroxide) initiator (Aldrich Chemical Company), together with 4 ml THF, followed by continued mixing for an additional 10 minutes. The polymer-initiator mixture was then removed from the mixer and compression molded at 145° C. for 90 minutes, resulting in the formation of a PI-PU IPN film. The film was maintained in a vacuum chamber for about 60 hours to ensure removal of THF.

The resulting PI-PU IPN had the following properties (shown in comparison to properties of a polyurethane homopolymer):

|  | PI-PU IPN | PU Homopolymer |
|---|---|---|
| Glass transition temperature, °C. | −60 and −45 (DSC) | −46 |
| Elastic modulus, MPa | 8.6 | 10.0 |
| Tensile strength (true), MPa | 339 | 246 |
| Toughness, MJ m$^3$ | 135 | 110 |
| Ultimate strain (at break), % | 1,030 | 820 |

From the foregoing, it can be seen that the PI-PU IPN has a higher tensile strength, greater ultimate elongation, and greater toughness than the PU homopolymer.

Example 2—Based on Elastollan TPU

A polyisoprene-polyurethane interpenetrating polymer network (PI-PU IPN), having a ratio of PI to PU of about 1:9 by weight was prepared as follows:

A solution of BPO (benzoyl peroxide) and linear cis-1,4- PI (Aldrich Chem. Co.) (premasticated at 120° C.) was prepared in THF (tetrahydrofuran solvent) in the following concentrations (solution A):

cis-PI: 15% by wt. based on the total solution;
BPO: 1% by wt. based on cis-PI.

A solution was also made by mixing Elastollan TPU (BASF Corp.) with THF (Fisher Scientific Co.) in the following concentration (solution B):

Elastollan: 15% by wt. based on the total solution.

20.0 gm of solution A was mixed with 180.0 gm of solution B in a glass jar using vigorous mechanical stirring for approximately 30 minutes. The resulting mixture was then transferred to a vacuum chamber, equipped with a cold trap, for removing the dissolved air from the solution. After about 10 min. of degassing, the mold was transferred to a ventilated hood and the THF solvent allowed to evaporate at room temperature over the next 48 hours. The resulting film was turned upside down and allowed to dry another 24 hours. The film was then placed under vacuum for 96 hours at room temperature to remove any residual THF. Finally, the film was crosslinked by compression molding at 120° C. for 15 min.

The resulting IPN is sample no. 2 in Tables I and III.

We claim:

1. A process for producing a material which is a biocompatible elastomeric semi-interpenetrating polymer network of a polyurethane polymer and a polyisoprene polymer, said process comprising:

(a.) forming a mixture of:

(i.) a medical grade of a crystalline, physically crosslinked polyurethane polymer, which contains polyether elastomeric blocks alternating with urethane linkages or polyester elastomeric blocks alternating with urethane linkages, said polyurethane polymer having a variable amount of crystallinity, such that when said material is in a relaxed state, said polyurethane polymer is not fully crystalline and contains at least some non-physically crosslinked non-crystalline regions, and such that when said material is in a stretched or extended state, said polyurethane polymer is more crystalline than when said material is in said relaxed state, with said polyurethane polymer then containing a greater number of physically crosslinked crystalline regions, and further such that said amount of crystallinity of said polyurethane polymer is reversible as said material is alternated between said stretched or extended state and said relaxed state;

(ii.) a medical grade of linear, crystalline, chemically crosslinked polyisoprene polymer, said polyisoprene polymer having a variable amount of crystallinity, such that when said material is in a relaxed state, said polyisoprene polymer is crosslinked and is not fully crystalline, containing at least some non-crystalline regions, and such that when said material is in a stretched or extended state, said polyisoprene polymer is chemically crosslinked and is more crystalline than when said material is in said relaxed state, with said polyisoprene polymer then containing a greater number of chemically crosslinked crystalline regions, and further such that said amount of crystallization of said polyisoprene polymer is reversible as said material is alternated between said stretched or extended state and said relaxed state;

wherein both said polyurethane polymer and said polyisoprene polymer have morphologies such that they each exist in a co-continuous phase; and (iii.) an effective amount of polymerization initiator sufficient to crosslink said polyisoprene polymer; and (b.) compression-molding said mixture to form said semi-interpenetrating polymer network.

2. The process according to claim 1 wherein said polyurethane polymer and said polyisoprene polymer are both present as solutions in tetrahydrofuran solvent, with each solution containing about 15% by weight of the respective polymer.

3. The process according to claim 1 wherein said polyisoprene polymer and said polyurethane polymer are present in a ratio of from about 1:99 to about 99:1, by weight.

4. The process according to claim 1 wherein said polyisoprene polymer is a cis-polyisoprene.

5. The process according to claim 1 wherein said polyisoprene polymer is cis-1,4 polyisoprene.

6. The process according to claim 1 wherein said polyurethane polymer is a thermoplastic polyurethane.

7. The process according to claim 3 wherein said ratio of polyisoprene polymer to polyurethane polymer is from about 10:90 to about 40:60, by weight.

8. The process according to claim 1 wherein the polymerization initiator is selected from the group consisting of benzoyl peroxide and dicumyl peroxide.

9. The process according to claim 1 wherein compression-molding of said mixture is performed at a temperature of from about 100° C. to about 150° C.

10. The process according to claim 1 wherein said polymerization initiator is present in an amount of about 1% by weight of said polyisoprene polymer.

11. The process according to claim 1 wherein formation of the mixture of the polyurethane polymer and the polyisoprene polymer is accompanied by vigorous stirring.

12. The process according to claim 1 wherein compression-molding is performed in silicone-coated molds.

13. The process according to claim 2 further comprising the steps, performed between the step of forming said mixture of said polyurethane polymer, polyisoprene polymer and initiator, and the step of compression molding said mixture, of degassing said mixture to remove air and evaporating said solvent.

14. The process according to claim 13 wherein said degassing and evaporating steps are performed in a vacuum chamber.

15. The process according to claim 1 wherein when said polyurethane contains polyether elastomeric blocks, said polyether elastomeric blocks are selected from the group consisting of polyethylene glycol polyether, polypropyleneglycol polyether, and polytetramethylene glycol polyether.

* * * * *